(12) United States Patent
Zhang et al.

(10) Patent No.: US 11,596,344 B2
(45) Date of Patent: Mar. 7, 2023

(54) DEEP NEURAL NETWORK ON ECG POINCARE PLOT FOR ATRIAL FIBRILLATION CLASSIFICATION

(71) Applicant: TENCENT AMERICA LLC, Palo Alto, CA (US)

(72) Inventors: Shangqing Zhang, San Jose, CA (US); Min Tu, Cupertino, CA (US); Kun Wang, San Jose, CA (US); Xu Wang, Palo Alto, CA (US); Xiaozhong Chen, Cedarburg, WI (US); Wei Fan, New York, NY (US)

(73) Assignee: TENCENT AMERICA LLC, Palo Alto, CA (US)

( * ) Notice: Subject to any disclaimer, the term of this patent is extended or adjusted under 35 U.S.C. 154(b) by 625 days.

(21) Appl. No.: 16/668,532

(22) Filed: Oct. 30, 2019

(65) Prior Publication Data
US 2021/0128004 A1    May 6, 2021

(51) Int. Cl.
*A61B 5/00* (2006.01)
*A61B 5/361* (2021.01)
*G06N 3/04* (2023.01)
*G16H 50/20* (2018.01)
*A61B 5/352* (2021.01)

(52) U.S. Cl.
CPC .............. *A61B 5/361* (2021.01); *A61B 5/352* (2021.01); *A61B 5/7264* (2013.01); *G06N 3/04* (2013.01); *G16H 50/20* (2018.01)

(58) Field of Classification Search
CPC combination set(s) only.
See application file for complete search history.

(56) References Cited

U.S. PATENT DOCUMENTS

| | | | | |
|---|---|---|---|---|
| 9,547,820 | B2* | 1/2017 | Kim | G06N 3/08 |
| 10,463,269 | B2* | 11/2019 | Boleyn | A61B 5/0006 |
| 10,602,942 | B2* | 3/2020 | Shakur | A61B 5/349 |
| 11,013,470 | B2* | 5/2021 | Shakur | A61B 5/332 |
| 11,083,371 | B1* | 8/2021 | Szabados | A61B 5/11 |
| 11,521,743 | B2* | 12/2022 | Wang | G06N 3/08 |
| 2007/0232945 | A1* | 10/2007 | Kleckner | A61N 1/3621 |
| | | | | 600/509 |

(Continued)

OTHER PUBLICATIONS

Vahid Houshyarifar et al., "Early detection of sudden cardiac death using Poincare plots and recurrence plot-based features from HRV signals", Turkish Journal of Electrical Engineering & Conputer Sciences, 2017, pp. 1541-1553, vol. 25.

(Continued)

*Primary Examiner* — Shirley X Jian
(74) *Attorney, Agent, or Firm* — Sughrue Mion, PLLC

(57) ABSTRACT

A method, computer program, and computer system for detecting and classifying atrial fibrillation by receiving data corresponding to an electrocardiogram (ECG) associated with a patient, extracting RR intervals from the received ECG data, determining previous RR intervals for each of the extracted RR intervals and aggregating features associated with the RR intervals and the previous RR intervals. Patterns associated with the aggregated features are classified, and the computer may determine that a sample of the ECG data corresponding to one or more of the classified patterns contains a pattern associated with atrial fibrillation.

20 Claims, 7 Drawing Sheets

(56) References Cited

U.S. PATENT DOCUMENTS

| | | | | |
|---|---|---|---|---|
| 2013/0117207 A1* | 5/2013 | Kim | ............... | G06N 3/08 706/20 |
| 2019/0090769 A1* | 3/2019 | Boleyn | ............... | A61B 5/0022 |
| 2019/0133468 A1* | 5/2019 | Aliamiri | ............... | A61B 5/7221 |
| 2020/0022660 A1* | 1/2020 | Sha | ............... | A61B 5/055 |
| 2020/0312459 A1* | 10/2020 | Li | ............... | G06N 3/0454 |

OTHER PUBLICATIONS

Paolo Melillo et al., "Automatic Prediction of Cardiovascular and Cerebrovascular Events Using Heart Rate Variability Analysis", Plos One, Mar. 20, 2015.

Pranaw Rajpurkar et al., "Cardiologist-Level Arrhythmia Detection with Convolutional Neural Networks", Jul. 6, 2017.

Peter Mell et al., "The NIST Definition of Cloud Computing", NIST Special Publication 800-145, Sep. 2011.

\* cited by examiner

DEEP NEURAL NETWORK ON ECG POINCARE PLOT FOR ATRIAL FIBRILLATION CLASSIFICATION

BACKGROUND

This disclosure relates generally to field of medicine, and more particularly to detection and classification of atrial fibrillation (AFib).

An electrocardiogram (ECG or EKG) is a commonly used tool by doctors to detect potential heart disease in patients. An ECG is a graph of the voltage changes within a patient's chest over time that are generated as a result of the electrical activity of the heart. The graph consists of a waveform with three main components, the P wave, the QRS complex, and the T wave. The QRS complex consists of the Q wave, the R wave, and the S wave.

SUMMARY

Embodiments relate to a method, system, and computer readable medium for detecting and classifying atrial fibrillation. According to one aspect, a method for detecting and classifying atrial fibrillation is provided. The method may include receiving, by a computer, data corresponding to an electrocardiogram (ECG) associated with a patient. One or more RR intervals may be extracted by the computer from the received ECG data. The computer may determine one or more previous RR intervals for each of the extracted RR intervals and may aggregate one or more features associated with the one or more RR intervals and the one or more previous RR intervals. One or more patterns associated with the aggregated features with classified by the computer, and the computer may determine that a sample of the ECG data corresponding to one or more of the classified patterns contains a pattern associated with atrial fibrillation.

According to another aspect, a computer system for detecting and classifying atrial fibrillation is provided. The computer system may include one or more processors, one or more computer-readable memories, one or more computer-readable tangible storage devices, and program instructions stored on at least one of the one or more storage devices for execution by at least one of the one or more processors via at least one of the one or more memories, whereby the computer system is capable of performing a method. The method may include receiving, by a computer, data corresponding to an electrocardiogram (ECG) associated with a patient. One or more RR intervals may be extracted by the computer from the received ECG data. The computer may determine one or more previous RR intervals for each of the extracted RR intervals and may aggregate one or more features associated with the one or more RR intervals and the one or more previous RR intervals. One or more patterns associated with the aggregated features with classified by the computer, and the computer may determine that a sample of the ECG data corresponding to one or more of the classified patterns contains a pattern associated with atrial fibrillation.

According to yet another aspect, a computer readable medium for detecting and classifying atrial fibrillation is provided. The computer readable medium may include one or more computer-readable storage devices and program instructions stored on at least one of the one or more tangible storage devices, the program instructions executable by a processor. The program instructions are executable by a processor for performing a method that may accordingly include receiving, by a computer, data corresponding to an electrocardiogram (ECG) associated with a patient. One or more RR intervals may be extracted by the computer from the received ECG data. The computer may deter mine one or more previous RR intervals for each of the extracted RR intervals and may aggregate one or more features associated with the one or more RR intervals and the one or more previous RR intervals. One or more patterns associated with the aggregated features with classified by the computer, and the computer may determine that a sample of the ECG data corresponding to one or more of the classified patterns contains a pattern associated with atrial fibrillation.

BRIEF DESCRIPTION OF THE DRAWINGS

These and other objects, features and advantages will become apparent from the following detailed description of illustrative embodiments, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
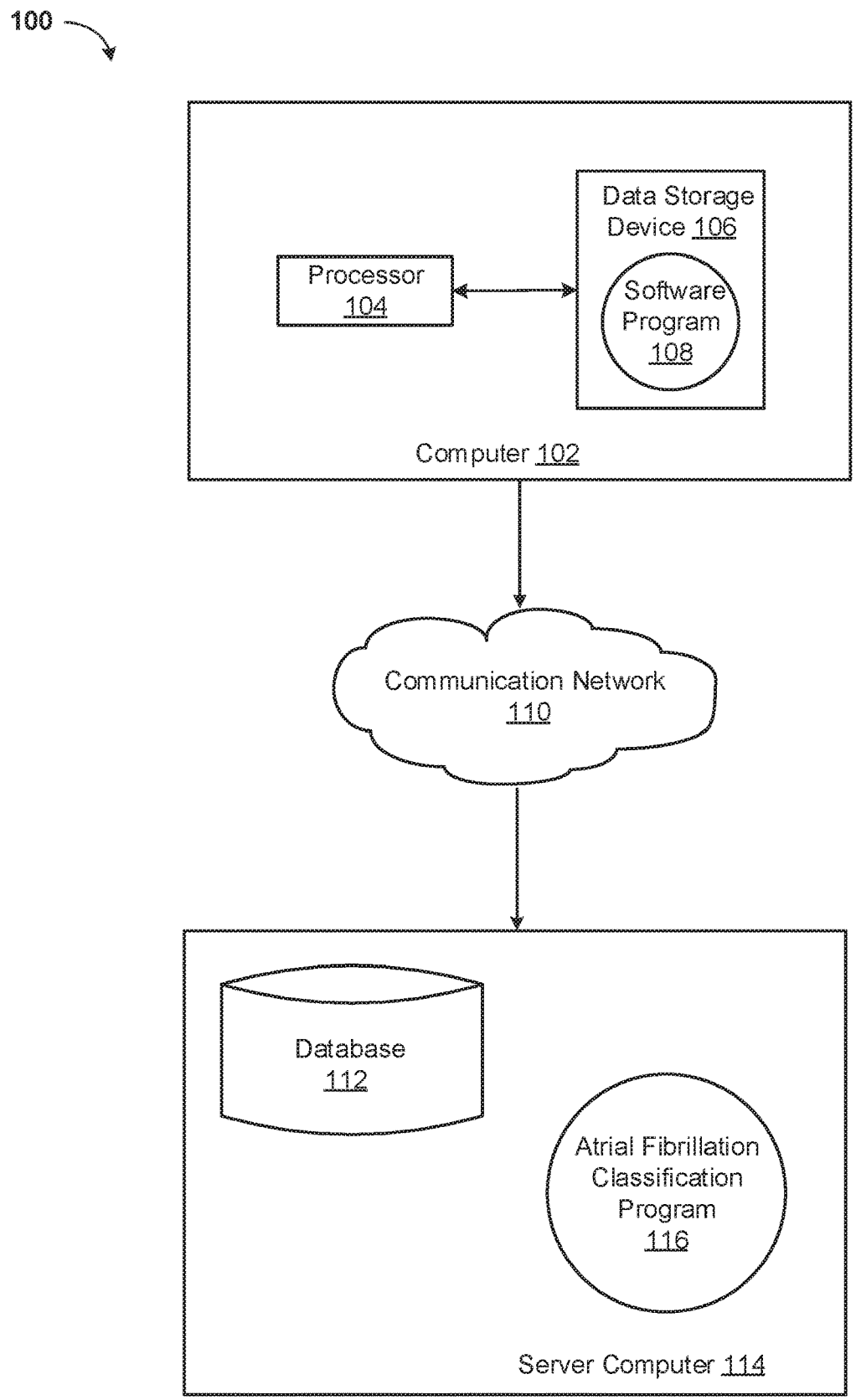
FIG. 1 illustrates a networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

Embodiments relate generally to the field of medicine, and more particularly to detecting and classifying atrial fibrillation. The following described exemplary embodiments provide a system, method and program product to, among other things, predict whether ECG data collected over a time interval contains a pattern associated with atrial fibrillation. Therefore, some embodiments have the capacity to improve the field of medicine by allowing for the use of deep neural networks to augment traditional medical clinical data. Thus, the computer-implemented method, computer system, and computer readable medium disclosed herein may, among other things, be used to make predictions on cardiac conditions, such as atrial fibrillation, and aid doctors in making a diagnosis in order to allow optimal and rapid treatment. Furthermore, while the method, system, and computer readable medium disclosed herein are described with respect to atrial fibrillation, the described embodiments may also be configured for the detection and classification of other arrhythmias, such as bradycardia, atrial tachycardia, supraventricular tachycardia, atrial flutter, ventricular tachycardia, and heart block.

As previously described, an electrocardiogram (ECG or EKG) is a commonly used tool by doctors to detect potential heart disease in patients. An ECG is a graph of the voltage changes within a patient's chest over time that are generated as a result of the electrical activity of the heart. The graph consists of a waveform with three main components, the P wave, the QRS complex, and the T wave. The QRS complex consists of the Q wave, the R wave, and the S wave. In an ECG, the interval between two successive R waves, or RR interval, can be used to measure of a patient's heart rate. Reading and analyzing an ECG may be an essential step in making a diagnosis for a patient. However, the occurrence of the heart risk patterns that may be found through an ECG can be highly unpredictable and may sometimes occur only rarely, even with a severe heart disease. A long-term ECG collection period, which may take 24-48 hours, may be required to discover underlying heart conditions, but this collection may yield data for hundreds of thousands of heartbeats that may be impossible to quickly analyze individually. Additionally, present methods may discard much of the raw ECG data.

It may be advantageous, therefore, to apply data analysis and statistical methods to highlight individual heartbeat patterns of concern out of the hundreds of thousands of heartbeats. Accordingly, the invention disclosed herein may improve the field of computing by providing a system, method, and program product to enable a computer to classify atrial fibrillation or other underlying cardiac conditions out of the hundreds of thousands of heartbeats to help doctors quickly parse ECG data to make a diagnosis. This classification may be performed by utilizing a large dataset to automatically learn any hidden correlations in the ECG data. By applying deep neural network methodologies, these patterns may be able to be discovered from the whole dataset itself without human bias in the design of the models while allowing for the preservation of as much of the raw ECG data as possible. By taking all the raw ECG data and using a deep neural network to convert sequential ECG data into a high-dimensional space, unintuitive features may be analyzed from the ECG data. Additionally, using a large dataset incorporating all the features in a deep neural network may provide an opportunity for the network to learn and improve in classification automatically.

Aspects are described herein with reference to flowchart illustrations and/or block diagrams of methods, apparatus (systems), and computer readable media according to embodiments of the invention. It will be understood that each block of the flowchart illustrations and/or block diagrams, and combinations of blocks in the flowchart illustrations and/or block diagrams, can be implemented by computer readable program instructions.

The following described exemplary embodiments provide a system, method and program product that detects and classifies atrial fibrillation in patients. According to the present embodiment, this detection and classification may be provided through analysis of raw ECG data through deep learning to detect heartbeat patterns associated with atrial fibrillation. Based on the detection of these patterns, the atrial fibrillation may be diagnosed and treated.

Referring now to FIG. 1, a functional block diagram of a networked computer environment illustrating an atrial fibrillation classification system 100 (hereinafter "system") for improved detection and classification of atrial fibrillation is shown. It should be appreciated that FIG. 1 provides only an illustration of one implementation and does not imply any limitations with regard to the environments in which different embodiments may be implemented. Many modifications to the depicted environments may be made based on design and implementation requirements.

The system 100 may include a computer 102 and a server computer 114. The computer 102 may communicate with the server computer 114 via a communication network 110 (hereinafter "network"). The computer 102 may include a processor 104 and a software program 108 that is stored on a data storage device 106 and is enabled to interface with a user and communicate with the server computer 114. As will be discussed below with reference to FIG. 5 the computer 102 may include internal components 800A and external components 900A, respectively, and the server computer 114 may include internal components 800B and external components 900B, respectively. The computer 102 may be, for example, a mobile device, a telephone, a personal digital assistant, a netbook, a laptop computer, a tablet computer, a desktop computer, or any type of computing devices capable of running a program, accessing a network, and accessing a database.

The server computer 114 may also operate in a cloud computing service model, such as Software as a Service (SaaS), Platform as a Service (PaaS), or Infrastructure as a Service (IaaS), as discussed below with respect to FIGS. 6 and 7. The server computer 114 may also be located in a cloud computing deployment model, such as a private cloud, community cloud, public cloud, or hybrid cloud.

The server computer 114, which may be used for detecting, classifying, and notifying a user of atrial fibrillation is enabled to run an Atrial Fibrillation Classification Program 116 (hereinafter "program") that may interact with a database 112. The Atrial Fibrillation Classification Program method is explained in more detail below with respect to FIG. 4. In one embodiment, the computer 102 may operate as an input device including a user interface while the program 116 may run primarily on server computer 114. In an alternative embodiment, the program 116 may run primarily on one or more computers 102 while the server computer 114 may be used for processing and storage of data used by the program 116. It should be noted that the program 116 may be a standalone program or may be integrated into a larger atrial fibrillation classification program.

It should be noted, however, that processing for the program 116 may, in some instances be shared amongst the computers 102 and the server computers 114 in any ratio. In another embodiment, the program 116 may operate on more than one computer, server computer, or some combination of computers and server computers, for example, a plurality of computers 102 communicating across the network 110 with a single server computer 114. In another embodiment, for example, the program 116 may operate on a plurality of server computers 114 communicating across the network 110 with a plurality of client computers. Alternatively, the program may operate on a network server communicating across the network with a server and a plurality of client computers.

The network 110 may include wired connections, wireless connections, fiber optic connections, or some combination thereof. In general, the network 110 can be any combination of connections and protocols that will support communications between the computer 102 and the server computer 114. The network 110 may include various types of networks, such as, for example, a local area network (LAN), a wide area network (WAN) such as the Internet, a telecommunication network such as the Public Switched Telephone Network (PSTN), a wireless network, a public switched network, a satellite network, a cellular network (e.g., a fifth generation (5G) network, a long-term evolution (LTE) network, a third generation (3G) network, a code division multiple access (CDMA) network, etc.), a public land mobile network (PLMN), a metropolitan area network (MAN), a private network, an ad hoc network, an intranet, a fiber optic-based network, or the like, and/or a combination of these or other types of networks.

The number and arrangement of devices and networks shown in FIG. 1 are provided as an example. In practice, there may be additional devices and/or networks, fewer devices and/or networks, different devices and/or networks, or differently arranged devices and/or networks than those shown in FIG. 1. Furthermore, two or more devices shown in FIG. 1 may be implemented within a single device, or a single device shown in FIG. 1 may be implemented as multiple, distributed devices. Additionally, or alternatively, a set of devices (e.g., one or more devices) of system 100 may perform one or more functions described as being performed by another set of devices of system 100.

Figure 2:
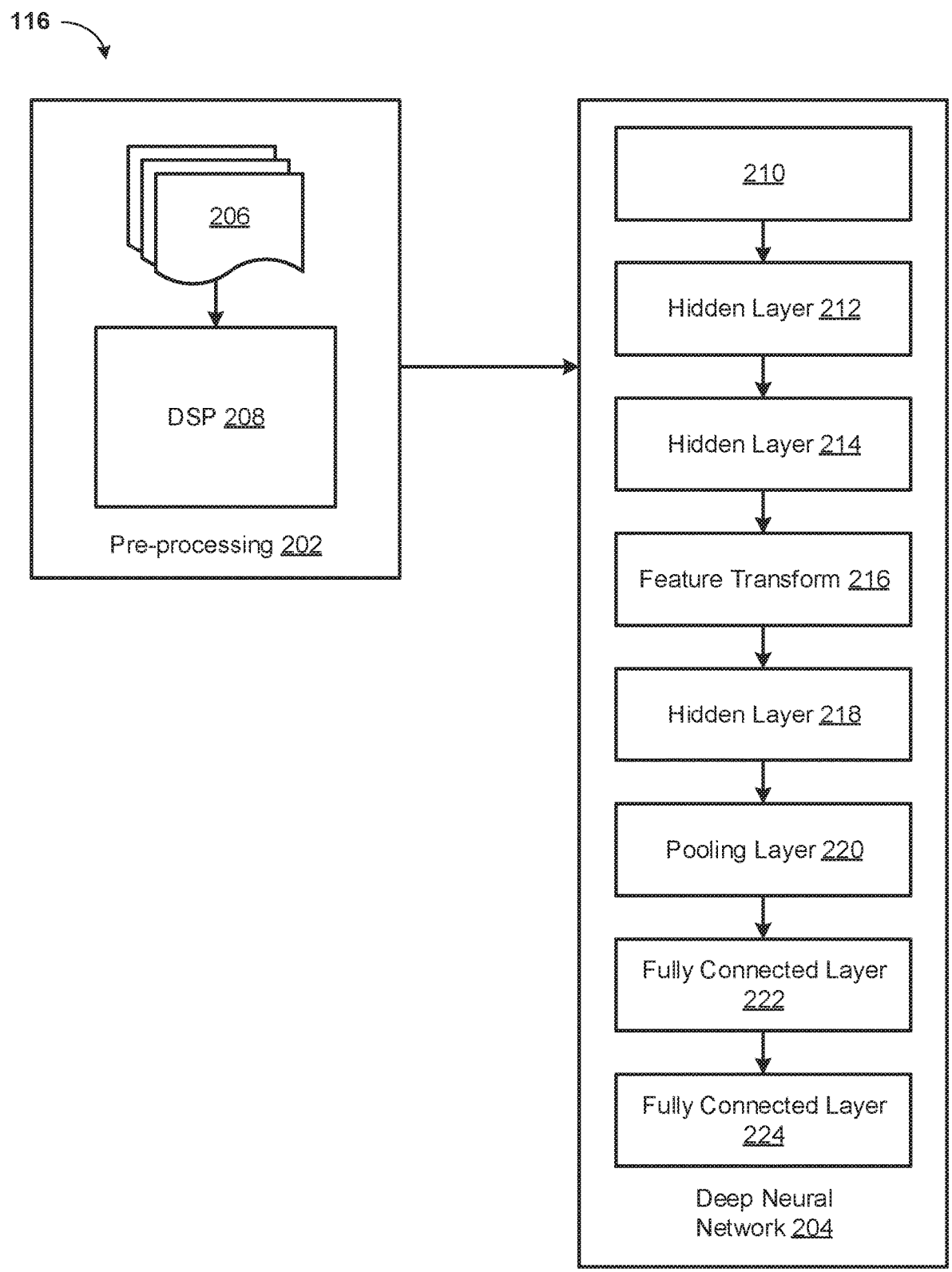
FIG. 2 is a block diagram of a program that detects and classifies atrial fibrillation, according to at least one embodiment.

Referring to FIG. 2, a block diagram of an Atrial Fibrillation Classification Program 116 is depicted. FIG. 2 may be described with the aid of the exemplary embodiments depicted in FIG. 1. According to one or more embodiments, the Atrial Fibrillation Classification Program 116 may be located on the computer 102 (FIG. 1) or on the server computer 114 (FIG. 1). The Atrial Fibrillation Classification Program 116 may accordingly include, among other things, a pre-processing module 202 and a deep neural network 204. The pre-processing module 202 may contain a digital signal processing (DSP) module 208 and may be configured to retrieve data 206. According to one embodiment, the data 206 may be retrieved from the data storage device 106 (FIG. 1) on the computer 102. In an alternative embodiment, the data 206 may be retrieved from the database 112 (FIG. 1) on the server computer 114. The data 206 may include, among other things, raw ECG data collected from a patient. According to one embodiment, the data 206 may be a full 24-48 hour, long-term collection period. According to an alternative embodiment, the data 206 may be a random sample of the collection period. According to still another alternative embodiment, the data 206 may be a sample of the collection period having a highest variance value. The DSP module 208 may extract one or more RR intervals from the data 206 by segmenting the data for each individual heartbeat. This may be accomplished, for example, by calculating a time interval between peaks of successive R waves. Thus, the DSP module 208 may, among other things, assist in converting a one-dimensional time signal corresponding to ECG data into a multi-dimensional array for processing by the deep neural network 204. The DSP module 208 may also apply data cleaning and filtering to the data 206 for better processing by the deep neural network 204.

The deep neural network 204 may include, among other things, an input matrix 210; one or more hidden layers 212, 214, and 218; a feature transform layer 216; a pooling layer 220; and one or more connected layers 222 and 224. It may be appreciated that FIG. 2 depicts only one implementation of a deep neural network 204, and that the deep neural network 204 is not limited to these exact layers and order of layers. The deep neural network 204 may contain any number of layers in any order, including adding or omitting any of the depicted layers.

The input matrix 210 may, for example, be a two-dimensional matrix with dimensions n by k, whereby n may be a number of RR intervals selected for analysis (i.e., the number of heartbeats) and k−1 may be a number of previous RR intervals for each of the RR intervals. For example, if 128 RR intervals were to be analyzed with a lookback window of three previous RR intervals for each of the 128 RR intervals, input matrix would have a size of 128 by 4. However, it may be appreciated that n and k may be any values that may be selected based on available computation power, such that more neighborhood information may be kept for each heartbeat for larger k values.

The feature transform layer 216 may be used to extract one or more features. The feature transform layer 216 is described in further detail with respect to FIG. 3. While only one feature transform layer 216 is depicted, it may be appreciated that the deep neural network 204 may contain additional feature transform layers 216 that may be applied to the data 206 in series or in parallel. The one or more hidden layers 212, 214, and 218 may be used to further process the data into a form usable by the deep neural network 204. The pooling layer 220 may be used to aggregate one or more features and down-sample the data analyzed for ease of identifying one or more features. The pooling layer 220 may apply a max-pooling strategy, an average-pooling strategy, or other pooling methods. The first fully connected layer 222 may be used, for example, to classify the aggregated features and to compare the features to one or more patterns. The patterns may be developed through deep learning, such that no human intervention may be present in the creation of the patterns. The second fully connected layer 224 may be used to classify whether the data 206 contains a pattern associated with atrial fibrillation by analyzing the output of the first fully connected layer 222. The second fully connected layer 224 may, for example, apply an indicator function to the data, such as outputting a "1" if the data contains a pattern associated with atrial fibrillation and outputting a "0" if the data does not. The deep neural network 204 may make an identification of the time period corresponding to a sample of the data that contains a pattern associated with atrial fibrillation. The deep neural network 204 may transmit the identified time period to a user, such that the user may, among other things, manually review the raw ECG data associated with that time period and make any relevant diagnoses, if applicable.

Figure 3:
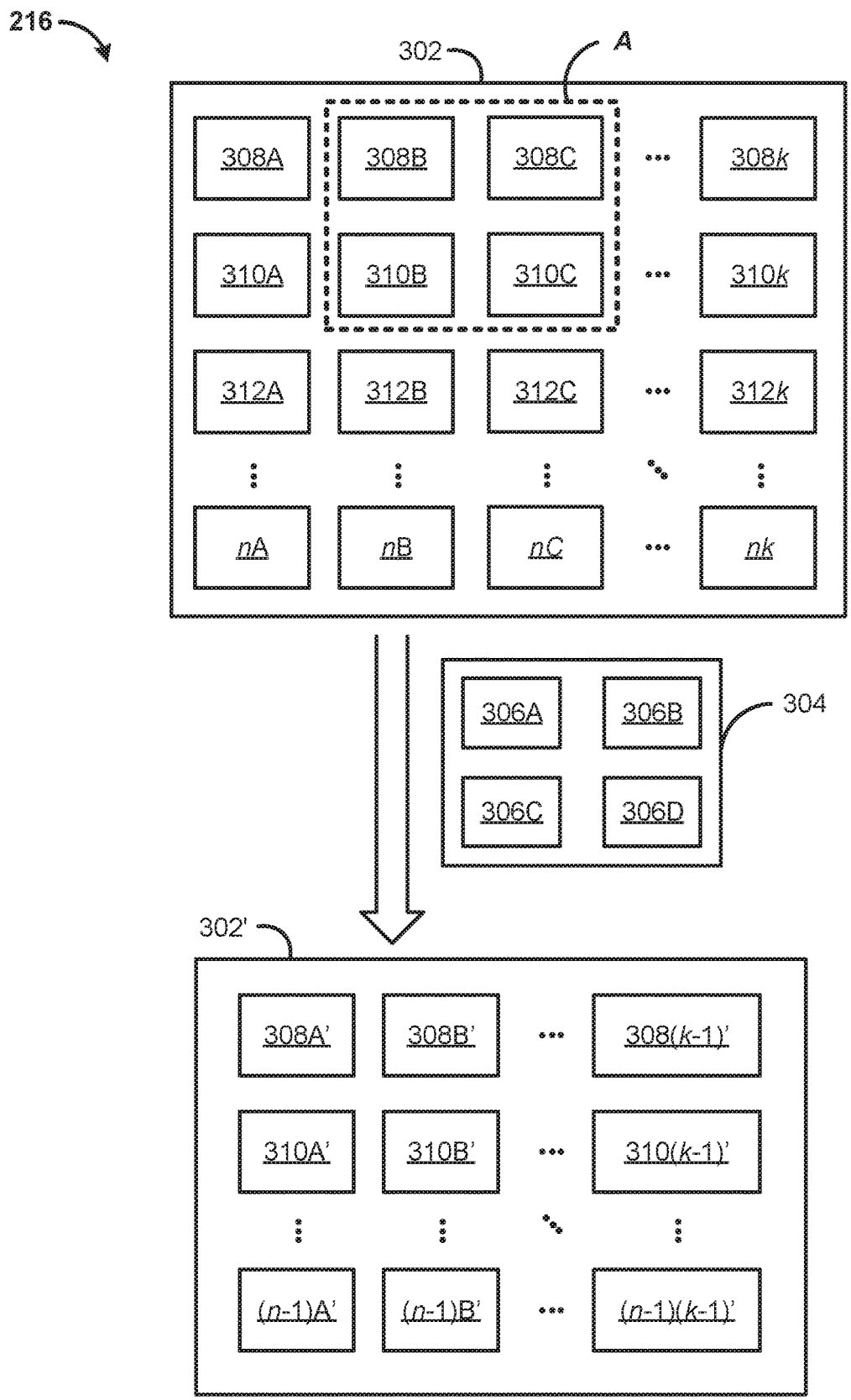
FIG. 3 is a functional block diagram of a feature transform filter as depicted in FIG. 2, according to at least one embodiment.

Referring now to FIG. 3, a function block diagram of an exemplary feature transform layer 216 is depicted, according to one or more embodiments. Feature transform layer 216 may contain a matrix 302 and a convolutional filter 304. By way of example and not of limitation, the convolutional filter 304 is depicted as a 2-by-2 matrix having four elements 306A-D. However, it may be appreciated that the convolutional filter 304 can be substantially any size with any number of elements. The matrix 302 may be, for example, a two-dimensional matrix having dimensions n by k, whereby n represents a number of heartbeats for analysis and k−1 represents a number of "lookback," or previous, heartbeats. Thus, heartbeat data 308A, 310A, and 312A through nA may be stored within the first column of matrix 302. Additionally, previous heartbeat data 308B-k, 310B-k, 312B-k, and nB-k associated with each of heartbeat data 308A, 310A, 312A, and nA, respectively, may be stored in columns two through k of matrix 302. For example, where heartbeat data 308A, 310A, and 312A correspond to sequential heartbeats, it may be appreciated that heartbeat data 308A, 310B, and 312C may be the same, substantially the same, or similar. The convolutional filter 304 may be applied to any or all of the component submatrices (e.g., submatrix A containing heartbeat data 3089, 308C, 310B, and 310C) of the matrix 302 having the same, substantially the same, or similar size as the convolutional filter 304. The matrix 302' may be generated as a result of calculating the scalar (i.e., dot) product of each of the component submatrices of the matrix 302 and the convolutional filter 304. For example, 308B' may be the dot product of submatrix A and the convolutional filter 304.

Figure 4:
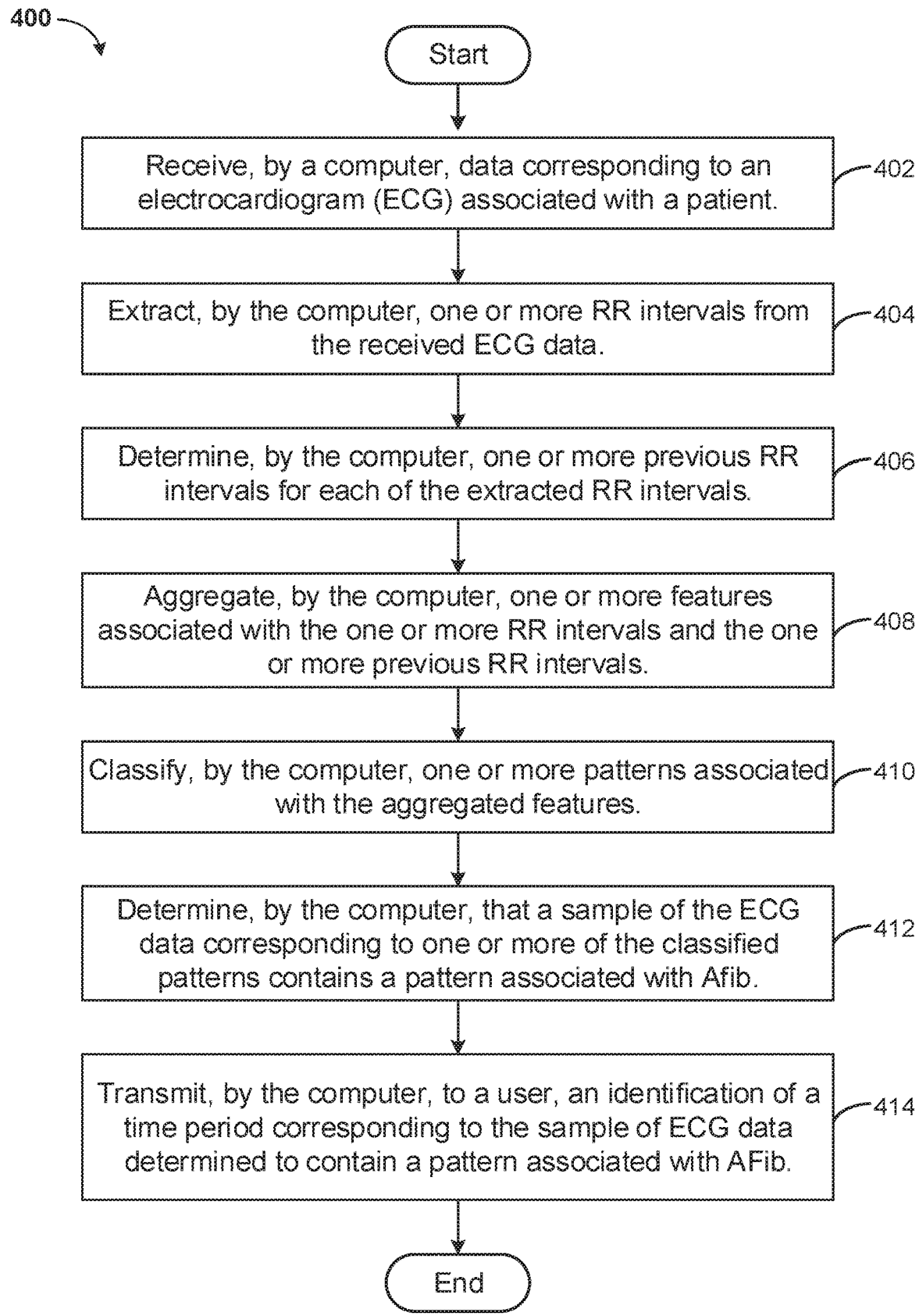
FIG. 4 is an operational flowchart illustrating the steps carried out by a program that detects and classifies atrial fibrillation, according to at least one embodiment.

Referring now to FIG. 4, an operational flowchart 400 illustrating the steps carried out by a program that detects and classifies atrial fibrillation is depicted. FIG. 4 may be described with the aid of FIGS. 1, 2, and 3. As previously described, the Atrial Fibrillation Classification Program 116 (FIG. 1) may quickly and effectively detect atrial fibrillation.

At 402, data corresponding to an electrocardiogram associated with a patient is received by a computer. The data may be a long-term ECG collection (i.e., 24-48 hours), a random sample of a long-term ECG collection, or a sample of a long-term ECG collection having a highest variance value. In operation, the Atrial Fibrillation Classification Program 116 (FIG. 1) may reside on the computer 102 (FIG. 1) or on the server computer 114 (FIG. 1). The Atrial Fibrillation Classification Program 116 may receive data 206 (FIG. 2) over the communication network 110 (FIG. 1) or may retrieve the data 206 from the database 112 (FIG. 1).

At 404, one or more RR intervals are extracted from the received ECG data by the computer. The ECG data may, for example, be received in the form of one-dimensional time data or a two-dimensional plot of voltage over time. Thus, extracting one or more RR intervals from the received ECG data may allow for a qualitative analysis of raw ECG data by obtaining segmentation data for each individual heartbeat from the ECG data. A number, n, of RR intervals may be stored in a column of an n by k two-dimensional matrix. The identification of the RR intervals may be, for example, calculating a time period between consecutive R waves and their respective local maxima. In operation, the DSP module 208 (FIG. 2) may identify one or more RR intervals corresponding to one or more heartbeats in the data 206 (FIG. 2). The DSP module 208 may, for example, store the data 206 in the first column of the input matrix 210 (FIG. 2).

At 406, one or more previous RR intervals are determined by the computer for each of the extracted RR intervals. The previous RR intervals may, among other things provide historical data for each of the RR intervals to be analyzed and may, for example, allow for the detection of unintuitive patterns to assist in diagnosing and treating atrial fibrillation. The previous RR intervals may be stored within the second and subsequent columns matrix. There may be, for example, k−1 previous RR intervals for each of the n RR intervals that may be stored in columns 2 through k of the two-dimensional matrix. In operation, the DSP module 208 (FIG. 2) may identify a number of previous heartbeat for each of the heartbeats present within the data 206 (FIG. 2). The DSP module 208 may store this information in the second and subsequent columns of input matrix 210 (FIG. 2).

At 408, one or more features associated with the one or more extracted RR intervals and the one or more previous RR intervals are aggregated by the computer. Because one or more convolutional filters may be applied to the data, it may be advantageous, for example, to down-sample the data by aggregating features in order to make processing the data more manageable and save on computing resources. In operation, the feature transform layer 216 (FIG. 2) may apply a convolutional filter 304 (FIG. 3) to the matrix 302 (FIG. 3). The convolutional filter 304 may be, for example, a size 2-by-2 array and may be applied to matrix 302 by calculating a dot product for each of the component 2-by-2 arrays of the matrix 302. Thus, a matrix 302' (FIG. 3) having a size (k−1)-by-(n−1) may be produced as a result of applying the convolutional filter 304 to the matrix 302. It may be appreciated that one or more convolutional filters 304 may be applied to the matrix 302 simultaneously, yielding one or more matrices 302'. These matrices 302' may be appended to one another by, for example, the hidden layer 218 (FIG. 2) to create a higher-order multi-dimensional array. The pooling layer 220 (FIG. 2) may apply one or more pooling strategies to the matrix 302', such as max-pooling or average-pooling. For example, the pooling layer 220 may apply max-pooling to the matrix 302' such that the maximum value present in each non-overlapping 2-by-2 component submatrix of the matrix 302' may be placed into a cell in a matrix having an approximate size (n−1)/2-by-(k−1)/2.

At 410, one or more patterns associated with the aggregated features are classified by the computer. After the features have been aggregated, the system may identify one or more patterns from among the features. These patterns may include features associated with a normal sinus rhythm, atrial fibrillation and other arrhythmias, such as bradycardia, atrial tachycardia, supraventricular tachycardia, atrial flutter, ventricular tachycardia, and heart block. In operation, the first fully connected layer 222 (FIG. 2) of the deep neural network 204 (FIG. 2) may analyze the down-sampled matrix output by the pooling layer 220 (FIG. 2) to determine if any patterns consistent with cardiac arrhythmias, such as atrial fibrillation, are present within the data 206 (FIG. 2). If any patterns are detected, the system may accordingly classify them based on the presence of such patterns.

At 412, a determination is made by the computer that a sample of the ECG data corresponding to one or more of the classified patterns contains a pattern associated with atrial fibrillation. After determining the presence of one or more patterns present within the data, the computer may, among other things, determine whether one or more of these patterns correspond to atrial fibrillation. By learning, through patterns in the data, whether the data contains atrial fibrillation, identification of such a condition can be made without human intervention and without bias in the development of the model. In operation, the second fully connected layer 224 (FIG. 2) of the deep neural network 204 (FIG. 2) may apply a filter to the output of the first fully connected layer 222 (FIG. 2) to determine whether there exists a pattern in the data 206 that corresponds to atrial fibrillation. The second fully connected layer 224 may output, for example, a "1" if it determines that an atrial fibrillation pattern may be present with the data 206. The second fully connected layer 224 may additionally output, for example, a "0" if it determines that an atrial fibrillation pattern may not be present within the data 206.

At 414, an identification of a time period corresponding to the sample of ECG data that was determined to contain a pattern associated with atrial fibrillation is transmitted to a user by the computer. By determining the time period, a user may be able to determine relevant diagnostic criteria, such as onset and provocation. Moreover, by transmitting a time period to a user, a user would be enabled to, for example, manually review one or more samples of the ECG data for accuracy and to assist in making a correct diagnosis. In operation, the Atrial Fibrillation Classification Program 116 on the server computer 114 (FIG. 1) may transmit an identification of a time period containing a pattern associated with atrial fibrillation to the software program 108 (FIG. 1) on the computer 102 (FIG. 1) over the communication network 110 (FIG. 1).

It may be appreciated that FIG. 4 provides only an illustration of one implementation and does not imply any limitations with regard to how different embodiments may be implemented. Many modifications to the depicted environments may be made based on design and implementation requirements. For example, as discussed above, in addition to assisting with the diagnosis and treatment of atrial fibrillation, the method, computer system, and computer readable medium disclose herein may be used for the diagnosis and treatment of other cardiac arrhythmias, such as bradycardia, atrial tachycardia, supraventricular tachycardia, atrial flutter, ventricular tachycardia, and heart block.

Figure 5:
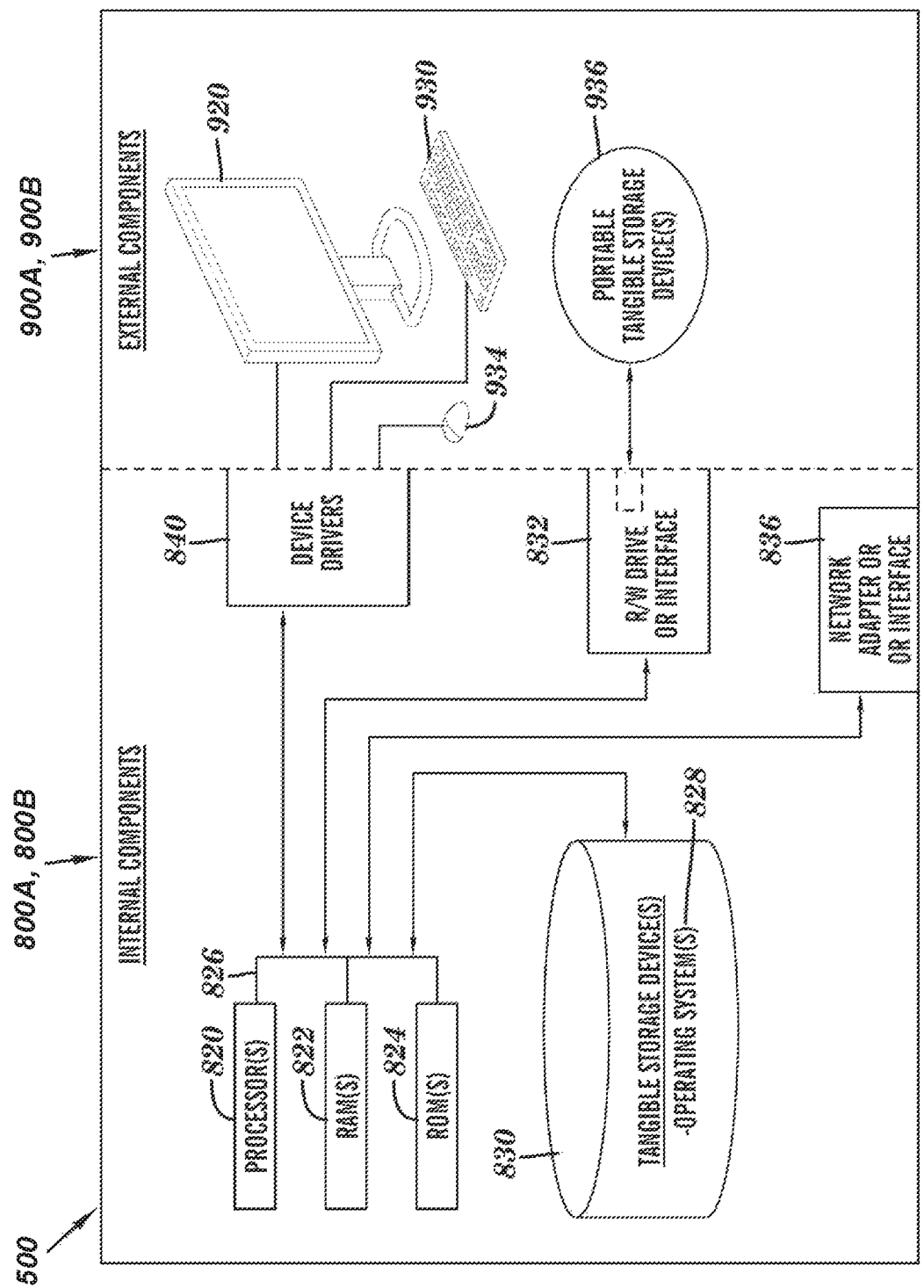
FIG. 5 is a block diagram of internal and external components of computers and servers depicted in FIG. 1 according to at least one embodiment.

FIG. 5 is a block diagram 500 of internal and external components of computers depicted in FIG. 1 in accordance with an illustrative embodiment. It should be appreciated that FIG. 5 provides only an illustration of one implementation and does not imply any limitations with regard to the environments in which different embodiments may be implemented. Many modifications to the depicted environments may be made based on design and implementation requirements.

Computer 102 (FIG. 1) and server computer 114 (FIG. 1) may include respective sets of internal components 800A,B and external components 900A,B illustrated in FIG. 5. Each of the sets of internal components 800 include one or more processors 820, one or more computer-readable RAMs 822 and one or more computer-readable ROMs 824 on one or more buses 826, one or more operating systems 828, and one or more computer-readable tangible storage devices 830.

Processor 820 is implemented in hardware, firmware, or a combination of hardware and software. Processor 820 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 820 includes one or more processors capable of being programmed to perform a function. Bus 826 includes a component that permits communication among the internal components 800A,B.

The one or more operating systems 828, the software program 108 (FIG. 1) and the Atrial Fibrillation Classification Program 116 (FIG. 1) on server computer 114 (FIG. 1) are stored on one or more of the respective computer-readable tangible storage devices 830 for execution by one or more of the respective processors 820 via one or more of the respective RAMs 822 (which typically include cache memory). In the embodiment illustrated in FIG. 5, each of the computer-readable tangible storage devices 830 is a magnetic disk storage device of an internal hard drive. Alternatively, each of the computer-readable tangible storage devices 830 is a semiconductor storage device such as ROM 824, EPROM, flash memory, an optical disk, a magneto-optic disk, a solid state disk, a compact disc (CD), a digital versatile disc (DVD), a floppy disk, a cartridge, a magnetic tape, and/or another type of non-transitory computer-readable tangible storage device that can store a computer program and digital information.

Each set of internal components 800A,B also includes a R/W drive or interface 832 to read from and write to one or more portable computer-readable tangible storage devices 936 such as a CD-ROM, DVD, memory stick, magnetic tape, magnetic disk, optical disk or semiconductor storage device. A software program, such as the software program 108 (FIG. 1) and the Atrial Fibrillation Classification Program 116 (FIG. 1) can be stored on one or more of the respective portable computer-readable tangible storage devices 936, read via the respective R/W drive or interface 832 and loaded into the respective hard drive 830.

Each set of internal components 800A,B also includes network adapters or interfaces 836 such as a TCP/IP adapter cards; wireless Wi-Fi interface cards; or 3G, 4G, or 5G wireless interface cards or other wired or wireless communication links. The software program 108 (FIG. 1) and the Atrial Fibrillation Classification Program 116 (FIG. 1) on the server computer 114 (FIG. 1) can be downloaded to the computer 102 (FIG. 1) and server computer 114 from an external computer via a network (for example, the Internet, a local area network or other, wide area network) and respective network adapters or interfaces 836. From the network adapters or interfaces 836, the software program 108 and the Atrial Fibrillation Classification Program 116 on the server computer 114 are loaded into the respective hard drive 830. The network may comprise copper wires, optical fibers, wireless transmission, routers, firewalls, switches, gateway computers and/or edge servers.

Each of the sets of external components 900A,B can include a computer display monitor 920, a keyboard 930, and a computer mouse 934. External components 900A,B can also include touch screens, virtual keyboards, touch pads, pointing devices, and other human interface devices. Each of the sets of internal components 800A,B also includes device drivers 840 to interface to computer display monitor 920, keyboard 930 and computer mouse 934. The device drivers 840, R/W drive or interface 832 and network adapter or interface 836 comprise hardware and software (stored in storage device 830 and/or ROM 824).

It is understood in advance that although this disclosure includes a detailed description on cloud computing, implementation of the teachings recited herein are not limited to a cloud computing environment. Rather, some embodiments are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 6:
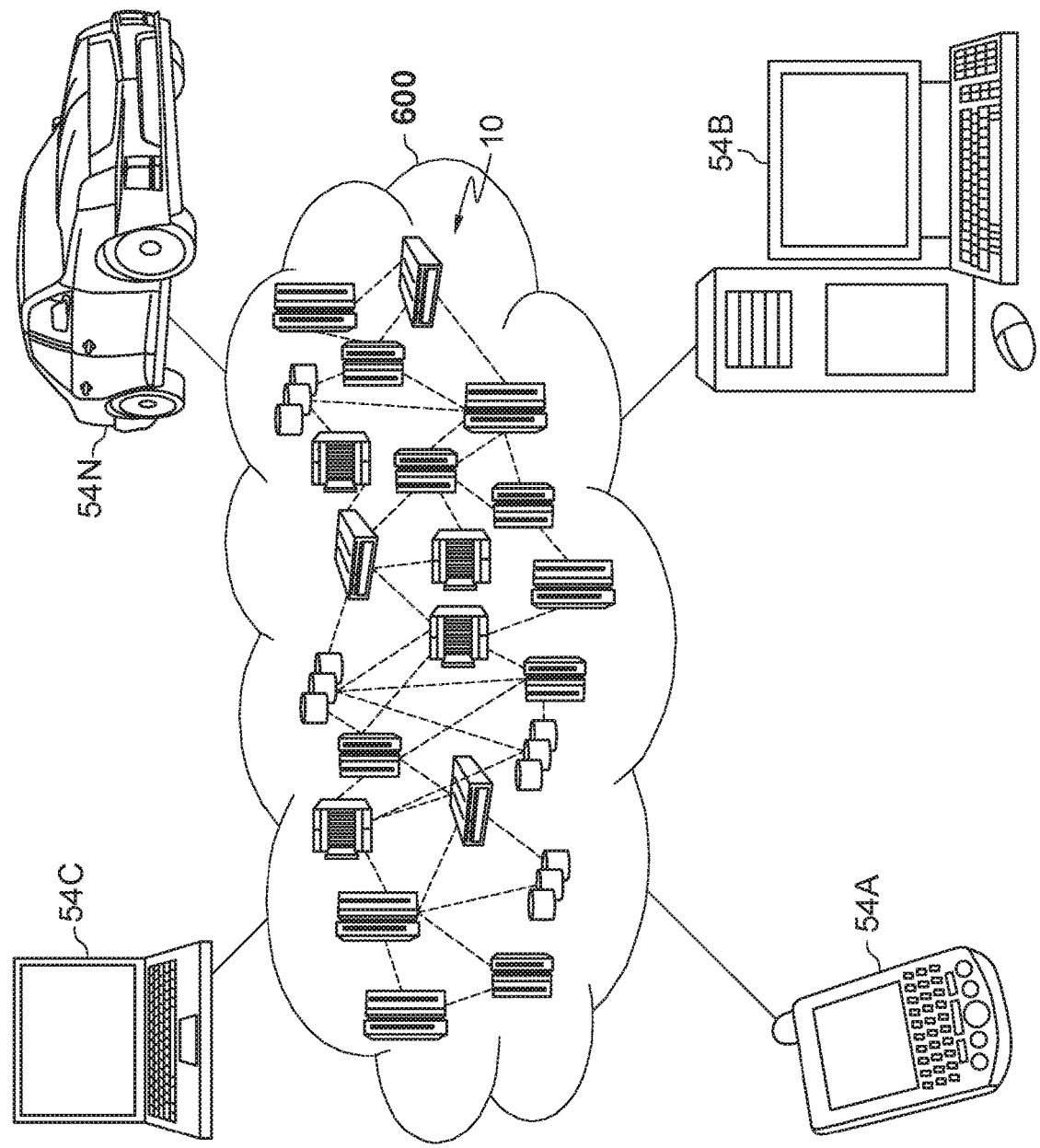
FIG. 6 is a block diagram of an illustrative cloud computing environment including the computer system depicted in FIG. 1, according to at least one embodiment.

Referring to FIG. 6, illustrative cloud computing environment 600 is depicted. As shown, cloud computing environment 600 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Cloud computing nodes 10 may communicate with one another. They may be grouped (not shown) physically or virtually, in one or more networks, such as Private, Community, Public, or Hybrid clouds as described hereinabove, or a combination thereof. This allows cloud computing environment 600 to offer infrastructure, platforms and/or software as services for which a cloud consumer does not need to maintain resources on a local computing device. It is understood that the types of computing devices 54A-N shown in FIG. 6 are intended to be illustrative only and that cloud computing nodes 10 and cloud computing environment 600 can communicate with any type of computerized device over any type of network and/or network addressable connection (e.g., using a web browser).

Figure 7:
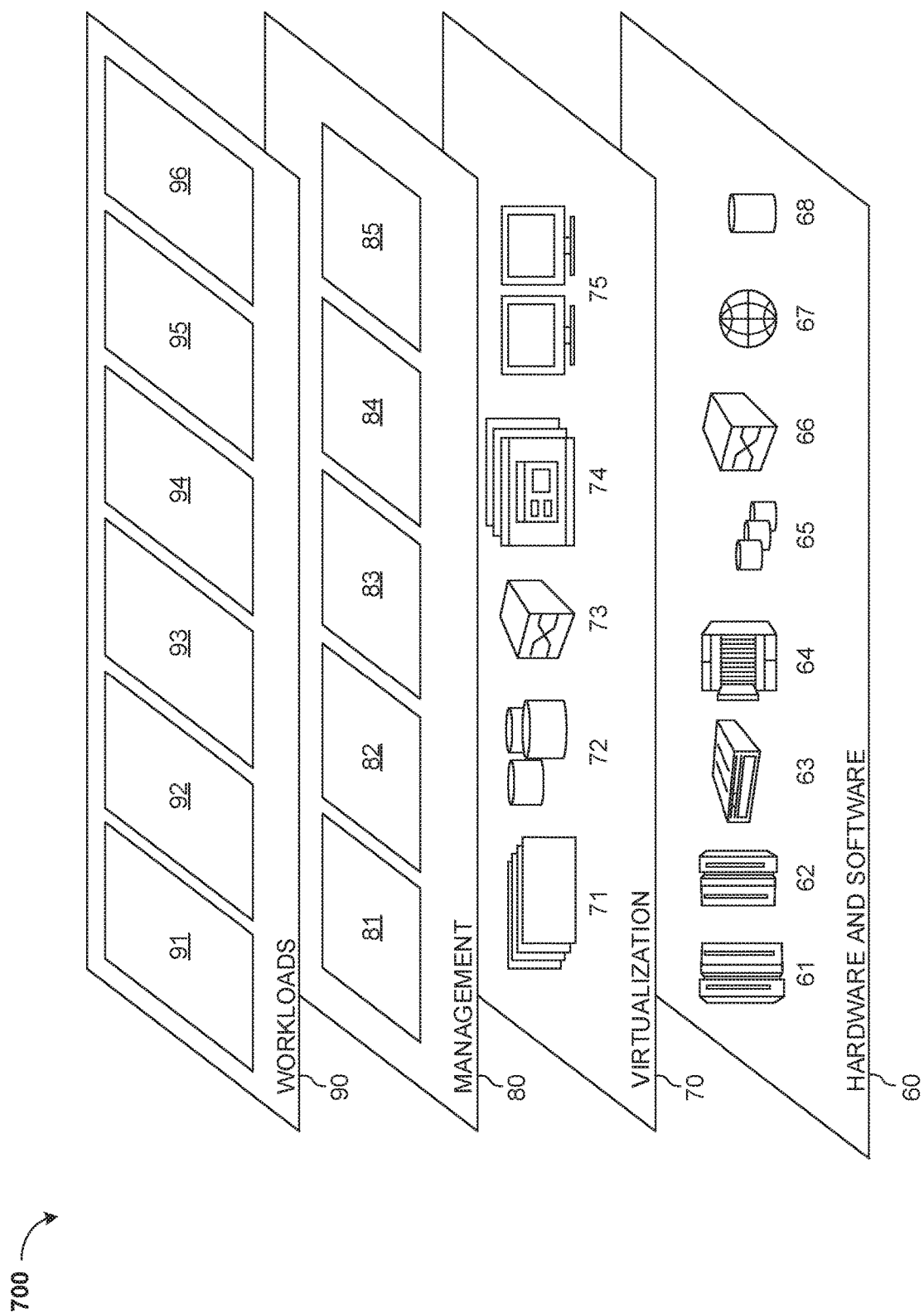
FIG. 7 is a block diagram of functional layers of the illustrative cloud computing environment of FIG. 6, according to at least one embodiment.

Referring to FIG. 7, a set of functional abstraction layers 700 provided by cloud computing environment 600 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and Atrial Fibrillation Classification 96. Atrial Fibrillation Classification 96 may detect and classify patterns associated with atrial fibrillation in a patient.

Some embodiments may relate to a system, a method, and/or a computer readable medium at any possible technical detail level of integration. The computer readable medium may include a computer-readable non-transitory storage medium (or media) having computer readable program instructions thereon for causing a processor to carry out operations.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program code/instructions for carrying out operations may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects or operations.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer readable media according to various embodiments. In this regard, each block in the flowchart or block diagrams may represent a module, segment, or portion of instructions, which comprises one or more executable instructions for implementing the specified logical function(s). The method, computer system, and computer readable medium may include additional blocks, fewer blocks, different blocks, or differently arranged blocks than those depicted in the Figures. In some alternative implementations, the functions noted in the blocks may occur out of the order noted in the Figures. For example, two blocks shown in succession may, in fact, be executed concurrently or substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

The descriptions of the various aspects and embodiments have been presented for purposes of illustration, but are not intended to be exhaustive or limited to the embodiments disclosed. Even though combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method of detecting and classifying atrial fibrillation (AFib), comprising:
    receiving, by a computer, data corresponding to an electrocardiogram (ECG) associated with a patient;
    extracting, by the computer, one or more RR intervals from the data;
    determining, by the computer, one or more previous RR intervals for each of the extracted RR intervals;
    aggregating, by the computer, one or more features associated with the one or more RR intervals and the one or more previous RR intervals into a two dimensional array comprising a first dimension, representing a number of the one or more RR intervals and the one or more previous RR intervals, and a second dimension representing a size of a lookback window of at least one of the one or more RR intervals;
    classifying, by the computer, one or more patterns associated with the aggregated features and based on a neural network that is trained based on ECG training data; and
    determining, by the computer, whether the data contains a pattern associated with AFib based on classifying the one or more patterns; and
    controlling a warning to be output based on determining that the data contains the pattern associated with AFib based on classifying the one or more patterns.

2. The method of claim 1, wherein the data is stored in the two dimensional array.

3. The method of claim 2, wherein the features are further aggregated by generating a multi-dimensional array in response to applying one or more convolutional filter layers to the two-dimensional array.

4. The method of claim 3, wherein determining whether the data comprises the pattern comprises applying a fully connected layer to the multi-dimensional array.

5. The method of claim 1, further comprising:
    transmitting, by the computer, to a user, an identification of a time period of the data based on classifying the one or more patterns.

6. The method of claim 1, wherein extracting the one or more RR intervals comprises:
    segmenting, by the computer, the data into a first and a second heartbeat; and
    calculating, by the computer, a time period between a first peak associated with a first R wave of the first heartbeat and a second peak associated with a second R wave of the second heartbeat.

7. The method of claim 1, wherein the aggregating comprises applying a max-pooling layer to the one or more RR intervals and the one or more previous RR intervals.

8. The method of claim 1, wherein the aggregating comprises applying an average-pooling layer to the one or more RR intervals and the one or more previous RR intervals.

9. The method of claim 1, wherein the data comprises ECG data collected from the patient over at least 24 hours.

10. The method of claim 1, wherein the data comprises variance between the one or more RR intervals and the one or more previous RR intervals.

11. A computer system for detecting and classifying atrial fibrillation (AFib), the computer system comprising:
    one or more computer-readable non-transitory storage media configured to store computer program code; and
    one or more computer processors configured to access said computer program code and operate as instructed by said computer program code, said computer program code including:
        receiving code configured to cause the one or more computer processors to receive data corresponding to an electrocardiogram (ECG) associated with a patient;
        extraction code configured to cause the one or more computer processors to extract one or more RR intervals from the data;
        determining code configured to cause the one or more computer processors to determine one or more previous RR intervals for each of the extracted RR intervals;
        aggregating code configured to cause the one or more computer processors to aggregate one or more features associated with the one or more RR intervals and the one or more previous RR intervals into a two dimensional array comprising a first dimension, representing a number of the one or more RR intervals and the one or more previous RR intervals, and a second dimension representing a size of a lookback window of at least one of the one or more RR intervals;

classifying code configured to cause the one or more computer processors to classify one or more patterns associated with the aggregated features and based on a neural network that is trained based on ECG training data;

pattern determining code configured to cause the one or more computer processors to determine whether the data contains a pattern associated with AFib based on classifying the one or more patterns; and controlling code configured to cause the one or more computer processors to control a warning to be output based on determining that the data contains the patter associated with AFib based on classifying the one or more patterns.

12. The computer system of claim 11, wherein the data is stored in the two dimensional array.

13. The computer system of claim 12, wherein the features are further aggregated by generating a multi-dimensional array in response to applying one or more convolutional filter layers to the two-dimensional array.

14. The computer system of claim 13, wherein determining whether the data comprises the pattern comprises applying a fully connected layer to the multi-dimensional array.

15. The computer system of claim 11, further comprising:
transmitting code configured to cause the one or more computer processors to transmit to a user, an identification of a time period of the data based on classifying the one or more patterns.

16. The computer system of claim 11, further comprising:
segmenting code configured to cause the one or more computer processors to segment the data into a first and a second heartbeat; and
calculating code configured to cause the one or more computer processors to calculate a time period between a first peak associated with a first R wave of the first heartbeat and a second peak associated with a second R wave of the second heartbeat.

17. The computer system of claim 11, wherein the aggregating comprises applying a max-pooling layer to the one or more RR intervals and the one or more previous RR intervals.

18. The computer system of claim 11, wherein the aggregating comprises applying an average-pooling layer to the one or more RR intervals and the one or more previous RR intervals.

19. The computer system of claim 11, wherein the data comprises variance between the one or more RR intervals and the one or more previous RR intervals.

20. A non-transitory computer readable media having stored thereon a computer program for detecting and classifying atrial fibrillation (AFib), the computer program configured to cause one or more computer processors to:

receive data corresponding to an electrocardiogram (ECG) associated with a patient;

extract one or more RR intervals from the data;

determine one or more previous RR intervals for each of the extracted RR intervals;

aggregate one or more features associated with the one or more RR intervals and the one or more previous RR intervals into a two dimensional array comprising a first dimension, representing a number of the one or more RR intervals and the one or more previous RR intervals, and a second dimension representing a size of a lookback window of at least one of the one or more RR intervals;

classify one or more patterns associated with the aggregated features and based on neural network that is trained based on ECG training data;

determine whether the data contains a pattern associated with AFib based on classifying the one or more patterns; and controlling a warning to be output based on determining that the data contains the patter associated with AFib based on classifying the one or more patterns.

* * * * *